(12) United States Patent
McGrath et al.

(10) Patent No.: US 9,174,014 B2
(45) Date of Patent: Nov. 3, 2015

(54) INTRODUCER GUIDE

(75) Inventors: Matthew J. R. McGrath, Edinburgh (GB); Peter Douglas Colin Inglis, Edinburgh (GB)

(73) Assignee: AIRCRAFT MEDICAL LIMITED, Edinburgh (GB)

( * ) Notice: Subject to any disclaimer, the term of this patent is extended or adjusted under 35 U.S.C. 154(b) by 203 days.

(21) Appl. No.: 13/254,575

(22) PCT Filed: Mar. 3, 2010

(86) PCT No.: PCT/GB2010/050378
§ 371 (c)(1),
(2), (4) Date: Nov. 15, 2011

(87) PCT Pub. No.: WO2010/100497
PCT Pub. Date: Sep. 10, 2010

(65) Prior Publication Data
US 2012/0065471 A1     Mar. 15, 2012

(30) Foreign Application Priority Data

Mar. 3, 2009    (GB) .................................. 0903743.3

(51) Int. Cl.
*A61B 1/267* (2006.01)
*A61M 16/04* (2006.01)

(52) U.S. Cl.
CPC ............ *A61M 16/0488* (2013.01); *A61B 1/267* (2013.01)

(58) Field of Classification Search
CPC ...... A61B 1/267; A61B 1/00052; A61B 1/04; A61B 1/0676; A61B 1/2673; A61B 1/0684; A61B 1/00105; A61B 1/00103; A61B 1/05; A61B 1/06; A61B 1/00045; A61B 1/00096; A61B 1/00101; A61B 1/015

USPC .................................. 600/184–188, 194, 114
See application file for complete search history.

(56) References Cited

U.S. PATENT DOCUMENTS

| | | | |
|---|---|---|---|
| 3,930,507 A | 1/1976 | Berman | |
| 4,069,820 A | 1/1978 | Berman | |
| 4,211,234 A * | 7/1980 | Fisher | 128/200.26 |
| 4,832,020 A | 5/1989 | Augustine | |
| 5,339,805 A * | 8/1994 | Parker | 128/200.26 |
| 6,672,305 B2 | 1/2004 | Parker | |
| 2002/0117171 A1 | 8/2002 | Parker | |
| 2003/0062039 A1 | 4/2003 | Sniadach | |

(Continued)

FOREIGN PATENT DOCUMENTS

| | | |
|---|---|---|
| CN | 201337437 | 11/2009 |
| JP | 07-505317 | 6/1995 |

(Continued)

OTHER PUBLICATIONS

International Search Report for PCT/GB2010/050378, mailed Jul. 16, 2010.
Office Action dated Dec. 31, 2013, issued in corresponding Chinese Application No. 201080020143.9 with English translation—18 pages.

(Continued)

*Primary Examiner* — Mary Hoffman
*Assistant Examiner* — Tara R Carter
(74) *Attorney, Agent, or Firm* — Nixon & Vanderhye PC

(57) ABSTRACT

An introducer guide (19) for an intubation device (21) having an open channel adapted to releasably secure an introducer, and shaped such that advancement of an intubation tube (21) through which the introducer extends causes the introducer to be removed from the introducer guide (19).

12 Claims, 4 Drawing Sheets

(56) References Cited

U.S. PATENT DOCUMENTS

2005/0126564 A1* 6/2005 Pekar .................. 128/200.26
2006/0276694 A1 12/2006 Acha

FOREIGN PATENT DOCUMENTS

| | | |
|---|---|---|
| JP | 2004-523306 | 8/2004 |
| JP | 2010-537684 | 12/2010 |
| WO | WO 2009/027669 | 3/2009 |

OTHER PUBLICATIONS

Office Action dated Jan. 28, 2014, issued in corresponding Japanese Application No. 2011-552523 with English translation—9 pages.

Office Action (5 pages) dated Dec. 9, 2014 issued in corresponding Japanese Application No. 2011-552523 and English translation (6 pages).

* cited by examiner

INTRODUCER GUIDE

This application is the U.S. national phase of International Application No. PCT/GB2010/050378, filed 3 Mar. 2010, which designated the U.S. and claims priority to GB Application No. 0903743.3, filed 3 Mar. 2009, the entire contents of each of which are hereby incorporated by reference.

FIELD OF THE INVENTION

The present invention relates to the field of introducer guides for assisting intubation procedures and intubation devices, such as laryngoscopes, including introducer guides.

BACKGROUND OF THE INVENTION

Endotracheal intubation, in which a tube is passed via the mouth or nose, through the larynx and into the trachea, is an important procedure in providing a positive airway in general medical practice to allow for the administration of anaesthesia or to provide air to the lungs. Endotracheal intubation may need to be performed for a variety of reasons, such as in the treatment of comatose patients where airways are liable to collapse due to reduced muscle tone, or, for example, in general anaesthesia wherein spontaneous respiration may be decreased or absent. In many of these cases, intubation tubes will need to be inserted by doctors or paramedics to unconscious patients in emergency situations. The procedure is further complicated by the risk of damage to the patient's teeth and the soft tissue of the throat. Considerable skill is therefore required when inserting an endotracheal tube in order to ensure that intubation is carried out in the quickest manner possible, without causing injury to the patient.

Endotracheal intubation is conventionally performed via direct laryngoscopy, in which a laryngoscope is used to restrain the patient's tongue and displace the epiglottis. This allows for direct visualisation of the larynx and the entrance to the trachea through the oral cavity, along with a clear passageway so that intubation may be more easily performed.

Traditional laryngoscopes comprise an elongate rigid blade, which may be curved or straight, extending from a handle, and typically include a light source, to illuminate the area of interest. In use, the laryngoscope blade is inserted through the oral cavity into the pharyngeal area, displacing the tongue and epiglottis. Once the laryngoscope is in position, an endotracheal tube is then inserted, via the nose or the oral cavity, alongside the laryngoscope blade and past the displaced epiglottis. Video laryngoscopes, employing a video camera located on or in the blade, or connected through a fibre optic bundle to a location on or in the blade, can provide further assistance when guiding the intubation tube into a patient's trachea.

Whilst visualisation of the intubation procedure has improved, the process of guiding the intubation tube into the trachea is still relatively cumbersome. The main problem with current intubation procedures is the difficulty in placing the tube. Various adjuncts, such as introducers, are known in the art for aiding this procedure as the introducer can be inserted prior to the more cumbersome intubating tube. However, there are still many cases where the introducer is accidentally placed into the oesophagus rather than the trachea, causing problems.

Introducers are firm guides, typically of small circumference, which are inserted into the larynx of the patient. Once the introducer is in place, the larger intubation tube is inserted over the introducer into the trachea. The introducer is then slidably removed from the trachea leaving the outer intubation tube in position. As introducers have some flexibility and/or malleability, they are particularly useful adjuncts to the intubation procedure when only part of the larynx is visible or when only the epiglottis can be seen. In use, the difference between the external diameter of the introducer and the internal diameter of the outer intubation tube should be fairly small as when greater differences between these diameters exist, the outer intubation tube can drag the introducer out of the airway. An example of a commonly used introducer is the Eschmann tracheal tube introducer (gum elastic bougie). This is a 60 cm long, 15 French Gauge flexible device with a J (coude) angle at its distal tip. This bougie can be passed into the trachea and, due to its flexible and malleable nature, is considered to be relatively atraumatic for the patient. The coude (bent) tip can also be used to sense the tracheal rings and thus to ensure that the bougie has not entered the oesophagus.

In order to direct the insertion of an intubation tube, it is known to provide guide means, for use with a laryngoscope blade. These guide means typically comprise a tube guide, for example, one or more channels which are of a sufficient diameter to house the intubation tube, and which are integrally formed with, or attached to the laryngoscope blade. Such guide channels typically extend along the majority of the length of the laryngoscope blade. It is also known from WO 2009/027669 (Aircraft Medical Limited) to provide a tube guide using spaced apart tube guiding members, reducing bulk.

In use, the intubation tube is inserted into the tube guide, and directed along its length into the trachea. Whilst this is a simple and effective means for introducing an intubation tube, in order to remove the laryngoscope and bougie once the intubation tube is in place, the laryngoscope blade must be slid back along the inserted tube towards the oral cavity, in order to separate the blade from the inserted tube. This is an awkward procedure as it requires the practitioner to hold both the laryngoscope and the inserted tube while withdrawing the blade, and can also be time-consuming, which is a significant disadvantage for a technique which is commonly used for medical procedures in which time can be of vital importance.

Furthermore, as the intubation tube is relatively large, some tube guides are very bulky. The size of the tube also obscures a user's view, even in cases where the laryngoscope is provided with video imaging, making insertion difficult. This is why introducers are often used to assist insertion but these are typically not guided into place.

The present invention provides improved guide means (such as a tube guide) which mitigates one or more of the limitations previously discussed.

Throughout this document the term blade portion should be read in a broad sense to cover not only laryngoscope blades but also to cover speculums or elements that are inserted into body cavities. Furthermore, whilst the term "bougie" is used throughout the specification, it will be understood that this is simply one example of a suitable introducer and that any suitable introducer is encompassed by the term.

SUMMARY OF THE INVENTION

According to a first aspect of the invention there is provided guide means (typically, an introducer guide) for an intubation device (for example, a laryngoscope), the guide means having an operating configuration in which the guide means defines an open channel adapted to releasably secure in position an introducer, the channel having first and second ends respectively upstream and downstream of the deployment direction of the introducer wherein the first end is shaped to contact an intubation tube so as to cause the intubation tube to remove the introducer from the guide means (typically, the introducer guide).

By the reference to an operating configuration we include the possibility that, in some embodiments, the guide means may have a plurality of configurations. For example, the guide means may also have a flattened configuration in which one or more members which define the open channel in the operating configuration are folded against a base portion of the guide means. However, the guide means may have only the operating configuration.

Thus, for the avoidance of doubt, the invention extends in a second aspect to a guide means (typically, an introducer guide) for an intubation device (for example, a laryngoscope), the guide means comprising an open channel adapted to releasably secure in position an introducer, the channel having first and second ends respectively upstream and downstream of the deployment direction of the introducer wherein the first end is shaped to contact an intubation tube so as to cause the intubation tube to remove the introducer from the guide means (typically, the introducer guide).

An intubation tube extends around the introducer in use (that is to say, the intubation tube has a bore and the introducer extends through the bore). The intubation tube may extend around the introducer when the introducer is first secured in the open channel. However, an intubation tube may be fitted around the introducer after the introducer has been secured in the open channel, and optionally after the introducer has been guided to its final location within a patient.

Advantageously, as the shaped first end of the guide means causes the intubation tube to contact the introducer and release it from the guide means, as the endotracheal tube is advanced, it removes the necessity to wrest the introducer from the guide means by alternative methods, such as by the medical practitioner imparting a violent sideways jerking motion which could result in injury to the patient.

Preferably the guide means comprises an open channel, which may be continuous or discontinuous. A discontinuous open channel may be defined by one or more suitable arranged (e.g. aligned) elements (e.g. tube guiding members).

Preferably, the guide means comprises a channel with a longitudinal portion which is permanently open. For example, the guide means may comprise an open channel defined by rigid walls.

The guide means comprises a channel with a longitudinal portion which is deformable such that it opens to release the introducer. For example, the guide means may comprise an elongate channel defined by walls, one or more of which are elastically deformable.

The guide means may comprise one or more walls which are deformable. For example, the guide means may be formed of an elastically deformable material (for example, it may comprise or consist of a tube guide defined by resilient walls). One or more walls may comprise or consist of a hinged guiding member. The hinged guiding member may be resiliently biased.

In this case, the material of the guide means can be deformed, allowing the guide means to hold the introducer in position, but to release the introducer upon the application of a gentle pressure as the intubation tube which surrounds the introducer pulls it away from the guide means. The guide means may be resiliently biased such that when the guide means is in the original undeformed state, the walls of the guide means are sufficiently close together to hold the introducer in position, and the guide means resiliently returns to this position once the introducer has been released such that the guide means can be reusable.

Optionally, the guide means is formed of a rigid or semi-rigid material.

However, the hinged guiding member may be operable between a flattened configuration in which the guide means cannot retain a tube guide and the operating configuration in which the hinged guiding member and at least one other guiding member (for example, a wall) together form guide means operable to releasably secure in position an introducer, the first end of which is shaped to contact an intubation tube so as to cause the intubation tube to remove the introducer from the guide means. This may enable a user to select whether to use the guide means (by putting the guide means into the operating configuration before use) or not (in which case, the hinged guiding member is conveniently stowed in a flattened configuration, minimising the bulk which it presents).

The first end of the guide means may comprise a tube deflecting formation operable to deflect an intubation tube through which an introducer retained with the guide extends as the intubation tube is advanced to engage with the tube deflecting formation.

The first end of the guide means may have a gradual incline. The first end of the guide means may comprise walls which extend at an angle of less than 60°, and preferably less than 45° or less than 30° to the length of the guide means. Preferably the first end of the guide means has a smooth taper.

Preferably, the internal diameter of the guide means is smaller than the outer diameter of the intubation tube.

Advantageously, as the internal diameter of the guide means is smaller than the outer diameter of the intubation tube, the intubation tube cannot enter into the guide means. Thus the continued forward motion of the intubation tube causes the course of the intubation tube to be diverted when it comes into contact with the shaped first end of the guide means.

The guide means may comprise means for attachment to a suitable medical device.

Preferably the medical device is a spatulate device. By spatulate device herein is meant any medical device having an element, such as a broad flat end, which can be inserted into a body cavity. The medical device is typically an intubation device, such as a laryngoscope. In this case, the intubation tube is typically an endotracheal tube. The laryngoscope may be a video laryngoscope comprising an imaging device (such as a video camera or a lens through which light is received and guided through fibre optics to a video camera) and the guide means may be arranged laterally of the imaging device so that the positioning of the introducer and advancement of an intubation tube distally of the blade portion may be observed during use.

Preferably, the means for attachment comprises a mating formation (for example, a groove) which enables it to be fitted to the blade portion of a suitable medical device (typically, by attachment to a cooperating formation on the blade portion). More preferably, the guide means comprises means for attachment to a laryngoscope blade.

Optionally, the guide means may be integrally formed with a medical device. The medical device is typically an intubation device and the guide means may be integrally formed with the blade portion of a laryngoscope. The blade portion may be integral with, or demountable from, a laryngoscope body.

Advantageously, as the device encourages separation of the introducer from the medical device in situ, there is no requirement to slide the device back along the tube towards the point of entry in order to remove the device once the tube is in position in the body cavity.

In a third aspect, the invention extends to a blade portion of an intubation device (for example a laryngoscope blade) and guide means according to the first or second aspect of the invention. The guide means may be demountably attachable to the blade portion. The guide means may be integral to the blade portion.

In a fourth aspect, the invention extends to an intubation device (typically a laryngoscope) and a blade portion according to the third aspect of the invention. The blade portion may be demountably attached to the intubation device (for example, the blade portion may be a disposable laryngoscope blade and the intubation device may be a reusable laryngoscope (e.g. video laryngoscope) body). The blade portion may be integral to the intubation device.

The invention extends in a fifth aspect to a kit comprising a guide means according to the first or second aspect of the invention, or a blade portion according to the third aspect of the invention, or an intubation device according to the fourth aspect of the invention; an introducer having a diameter sufficiently small to extend through the guide means (in the operating configuration where applicable) and an intubation tube (for example an endotracheal tube) having a diameter sufficiently large to not extend through the guide means.

In a sixth aspect, the invention extends to a method of intubating a patient, comprising the step of introducing an intubation device according to the fourth aspect of the invention into a patient, with an introducer extending through an intubation tube and the guide means, and then advancing an intubation tube towards the guide means such that the guide means causes the introducer to be removed from the guide means. Typically, the intubation device is then removed. The intubation device may be a laryngoscope, the intubation tube may be an endotracheal tube and the method may comprise the step of inserting the introducer into a patient's trachea before the endotracheal tube is advanced such that the guide means causes the introducer to be removed from the guide means.

BRIEF DESCRIPTION OF THE DRAWINGS

Embodiments of the invention will now be described, by way of example only, with reference to the accompanying drawings, in which.

Figure 1:
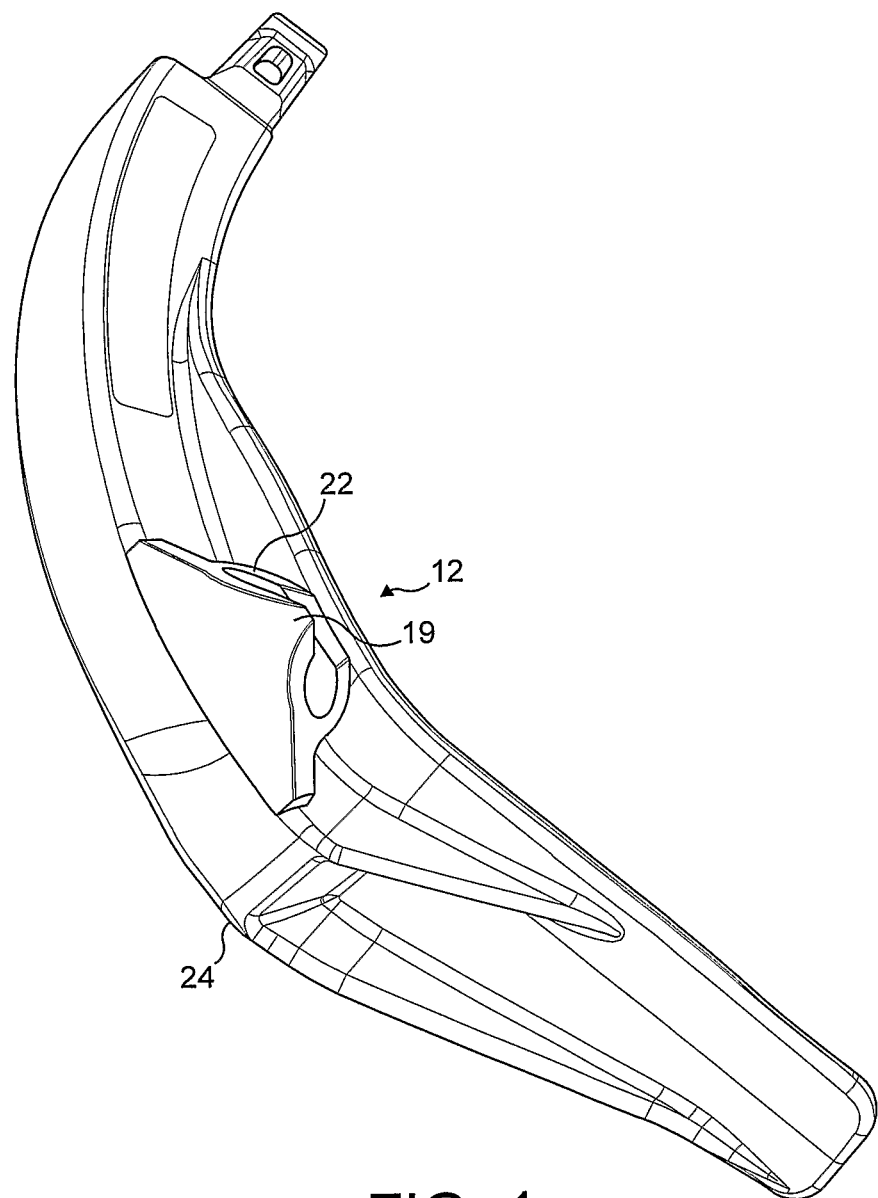
FIG. 1 is a perspective view of a laryngoscope blade comprising an introducer guide attached to the side of the blade according to an embodiment of the invention.

Referring firstly to FIG. 1, the drawing shows a blade portion 12 of a laryngoscope (being an example of an intubation device), with an introducer guide (functioning as guide means) 19 attached thereto. The introducer guide 19 includes a continuous channel, with an elongate longitudinal portion which is open to facilitate the gentle release of an introducer or bougie (not shown). The introducer guide 19 is resiliently deformable and in the non-deformed position, in which no force is being exerted on the channel, the open portion is slightly narrower than the outer diameter of the bougie such that it holds the bougie in position. The internal diameter of the channel is smaller than the outer diameter of the intubation tube being used (not shown). The first end 22 of the introducer guide 19 has a gentle taper, such that when the leading edge of the intubation tube comes into contact with the tapered first end 22 of the introducer guide 19, it diverts the intubation tube away from the blade portion 12, and gently eases the bougie from the introducer guide 19. In the depicted embodiment, the introducer guide 19 is positioned substantially near the point of curvature 24 of the blade portion 12, and is angled to guide a bougie 20 through the best approach into the larynx.

Figure 2:
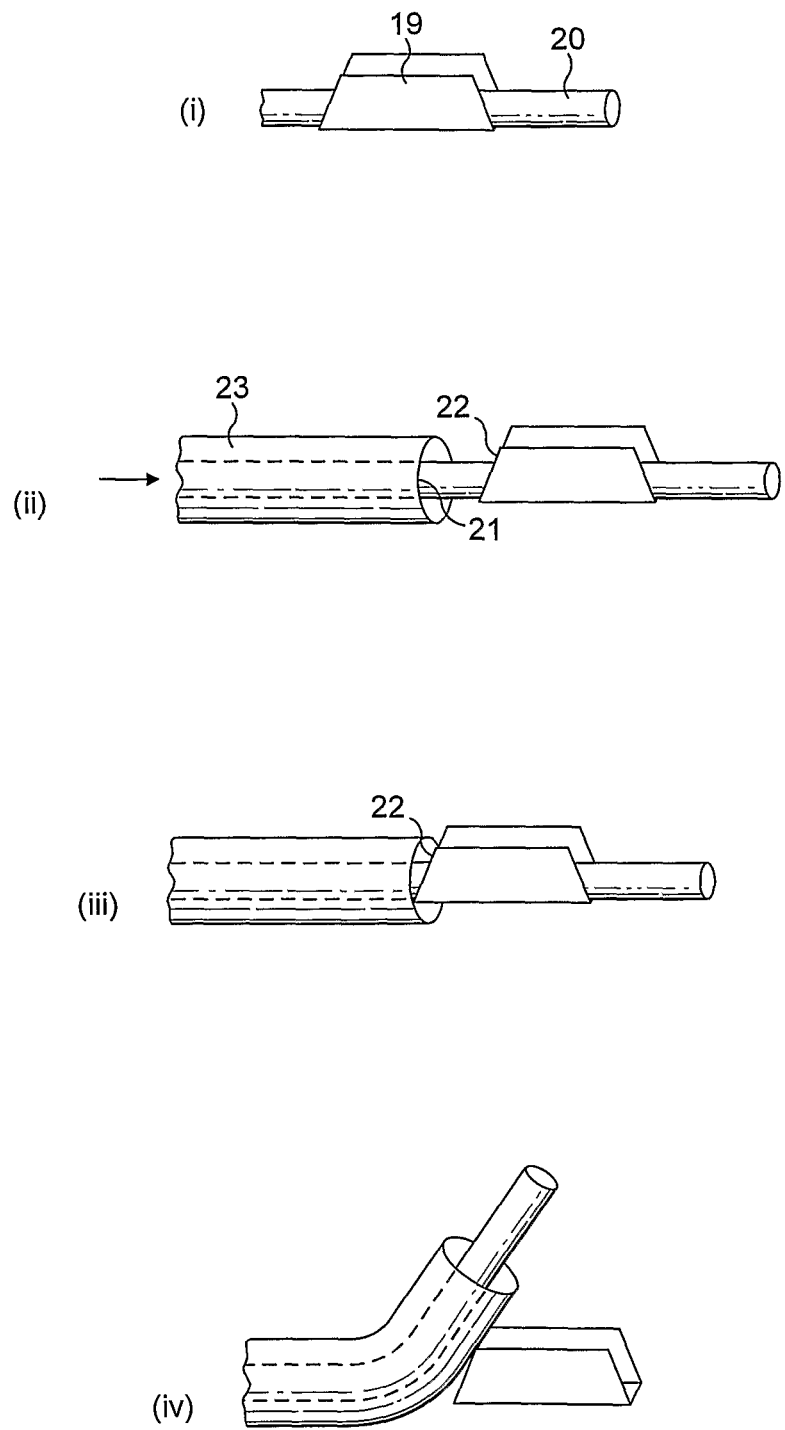
FIG. 2 is a schematic illustration of the introducer guide according to an embodiment of the invention in use.

A schematic depiction of the introducer guide in use is illustrated in FIG. 2. Prior to use, the bougie 20 is clipped into the introducer guide 19. In use, the blade portion (not shown) of a laryngoscope (not shown), is inserted through the oral cavity into the pharyngeal area, displacing the tongue and the epiglottis of the patient. The bougie 20 is then gently eased forward within the introducer guide 19 so that it is directed into position within the trachea of the patient. Once the bougie 20 is in place (FIG. 2(*i*)), the intubation tube 23 is guided along the bougie 20 within the throat (FIG. 2(*ii*)) until it comes into contact with the shaped first end 22 of the introducer guide 19 (FIG. 2(*iii*)). The contact between the leading edge of the intubation tube 21 and the tapered first end 22 of the introducer guide 19 causes the intubation tube 21 to be directed upwards. This causes the intubation tube 21 to contact the bougie 20, and to force the bougie upwards (FIG. 2(*iv*)). As the walls of the introducer guide 19 are slightly deformable, the force of the bougie 20 being moved upwards causes the introducer guide 19 to release the bougie 20.

Figure 3:
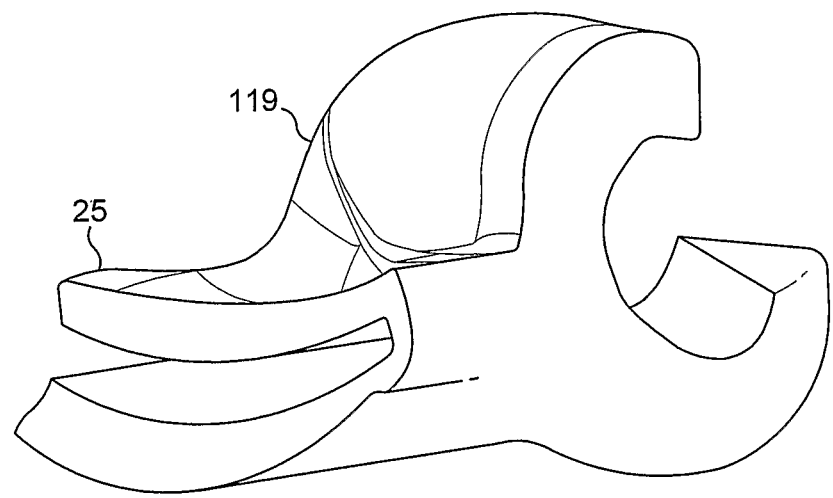
FIG. 3 is a perspective side view of an introducer guide which can be removably attached to a blade portion of a suitable medical device.

Referring now to FIG. 3, the drawing depicts another introducer guide 119 which can be removably attached to a blade portion of a laryngoscope of other intubation device. The introducer guide is generally depicted at 119 and forms a channel, with a longitudinal portion which is open to allow the bougie (not shown) to be released from the introducer guide 119 once in position. The introducer guide 119 comprises a clip portion 25 to allow it to be releasably attached to a surface of a blade portion of a suitable medical device.

Figure 4:
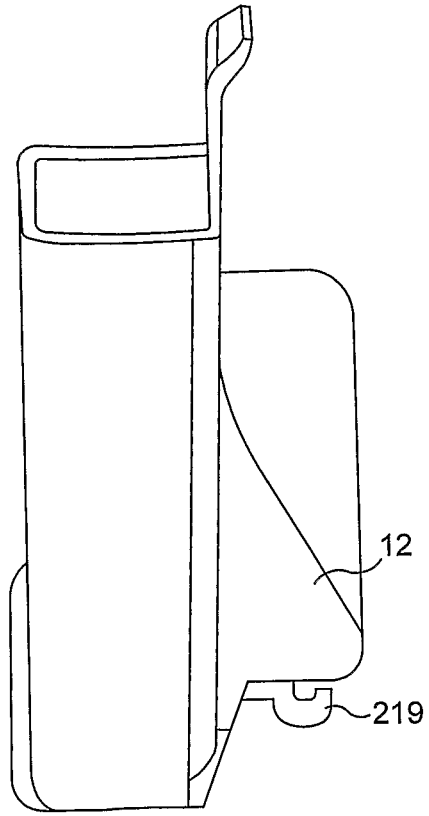
FIG. 4 is a rear perspective view of a preferred embodiment of the introducer guide attached to a blade portion of a medical device.

FIG. 4 depicts a introducer guide 219 which is attached to a blade portion 12 of a laryngoscope. The introducer guide is generally depicted at 219 and is the preferred embodiment. This embodiment generally works in the same way as the embodiment of FIG. 1 with the exception that when the introducer guide 219 is attached, either permanently or releasably, to a blade portion 12 of a suitable medical device, it forms a channel with a surface of the blade portion 12, suitable for receiving a bougie (not shown). This embodiment has the advantage that it is relatively cheap and easy to manufacture.

Figure 5A:
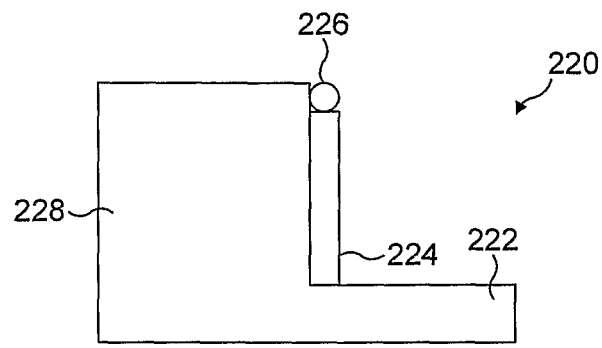
FIGS. 5A and 5B is a cross section though an introducer guide according to a further embodiment of the invention, in flattened and operating configurations respectively.
Figure 5B:
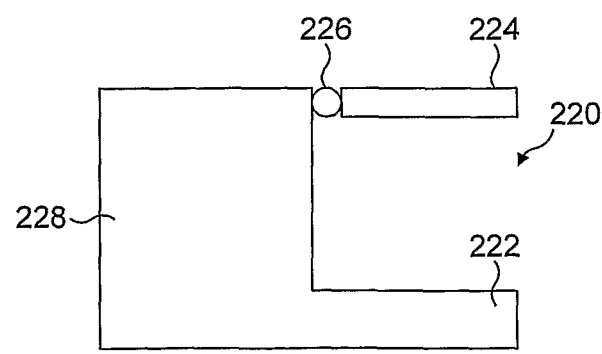

FIGS. 5A and 5B are cross-sections through introducer guide 220 having a flattened configuration (FIG. 5A) and an operating configuration (FIG. 5B). The introducer guide comprises a first wall 222 and a flap 224 which pivots about hinge 226 so that it has a low profile in the flattened configuration but functions as a second wall, opposing the first wall and defining an open channel, in the operating configuration. The tube guide is disposed laterally of a channel 228 which retains a video camera.

It can be seen that the current invention has a number of benefits over the prior art and a number of possible uses. Although the example above relates to a laryngoscope, it can be seen that the concept can be extended to other medical and veterinary devices and still stay within the scope of the present invention.

It will be appreciated by persons skilled in the art that the above embodiment has been described by way of example only, and not in any limiting sense, and that various alterations and modifications are possible without departure from the scope of the invention as defined by the appended claims.

The invention claimed is:

1. Introducer guide means for an intubation device, the introducer guide means having an operating configuration in which the introducer guide means defines an open channel adapted to releasably secure in position an introducer in the open channel, the channel having first and second ends respectively upstream and downstream of the deployment direction of the introducer wherein the first end is shaped to contact an intubation tube so as to cause the intubation tube to remove the introducer from the introducer guide means, the first end comprising a tube deflecting formation in the form of a smooth taper operable to deflect an intubation tube through which an introducer retained in the open channel of the introducer guide means extends as the intubation tube is advanced to engage with the tube deflecting formation.

2. Introducer guide means according to claim 1, also having a flattened configuration in which one or more members which define the open channel in the operating configuration are folded against a base portion of the introducer guide means.

3. Introducer guide means according to claim 1 wherein the open channel is elongate and is defined by walls, one or more of which are deformable.

4. Introducer guide means according to claim 3, wherein one or more walls are elastically deformable.

5. Introducer guide means according to claim 3, wherein one or more walls comprises or consists of a hinged guiding member.

6. Introducer guide means according to claim 1, wherein the first end of the introducer guide means comprises walls which extend at an angle of less than 60° to the length of the introducer guide means.

7. Introducer guide means according to claim 1, comprising means for attachment to a suitable medical device.

8. A blade portion of an intubation device and introducer guide means according to claim 1, said introducer guide means being demountably attachable to or integral to the blade portion.

9. An intubation device and a blade portion according to claim 8, said blade portion being demountably attachable to or integral to the intubation device.

10. An intubation device according to claim 9, which is a laryngoscope.

11. A method of intubating a patient, comprising the step of introducing an intubation device according to claim 9 into a patient, with an introducer extending through an intubation tube and the introducer guide means, and then advancing an intubation tube towards the introducer guide means such that the introducer guide means causes the introducer to be removed from the introducer guide means.

12. A kit comprising apparatus according to claim 1 and an intubation tube having a diameter sufficiently large to not extend through the introducer guide means.

* * * * *